United States Patent [19]
Portnoy

[11] 3,991,768
[45] Nov. 16, 1976

[54] SHUNT SYSTEM RESISTANT TO OVERDRAINAGE AND SIPHONING AND VALVE THEREFOR

[76] Inventor: Harold D. Portnoy, 1431 Woodward Ave., Bloomfield Hills, Mich.

[22] Filed: June 25, 1975

[21] Appl. No.: 590,079

Related U.S. Application Data

[63] Continuation of Ser. No. 342,039, March 16, 1973, abandoned.

[52] U.S. Cl. .............................. 128/350 V; 137/510; 251/5
[51] Int. Cl.² ........................................ A61M 27/00
[58] Field of Search ............ 128/350 R, 350 V, 274, 128/228, 276; 137/510, 525; 251/5, 342

[56] References Cited
UNITED STATES PATENTS

| | | | |
|---|---|---|---|
| 2,706,101 | 4/1955 | Cantor | 251/342 X |
| 2,707,074 | 4/1955 | Tussey | 137/525 X |
| 2,988,103 | 6/1961 | Canvasser | 251/5 X |
| 3,298,391 | 1/1967 | Savage | 251/5 X |
| 3,469,582 | 9/1969 | Jackson | 128/276 |
| 3,626,959 | 12/1971 | Santomieri | 251/342 X |
| 3,717,174 | 2/1973 | Dewall | 251/5 X |
| 3,768,508 | 10/1973 | Schulte | 137/525 X |
| 3,769,982 | 11/1973 | Schulte | 128/350 V |
| 3,833,013 | 9/1974 | Leonard | 128/214 R X |
| 3,901,245 | 8/1975 | Spitz et al. | 128/350 V |

*Primary Examiner*—Dalton L. Truluck
*Attorney, Agent, or Firm*—Donald D. Mon

[57] ABSTRACT

A physiological shunt system for draining fluid from one region of the human body and discharging it into another in which means is included to resist overdrainage or siphoning of the region as a consequence of low downstream pressures, and a valve to provide such means. The system includes a collector catheter and a discharge catheter, and the valve interconnects these catheters to open the system to flow, or to close it to flow, as a consequence of the position of its closure means which is responsive to the pressure differential between the pressure in the valve as transmitted by the catheters, and a reference pressure such as the atmosphere.

12 Claims, 14 Drawing Figures

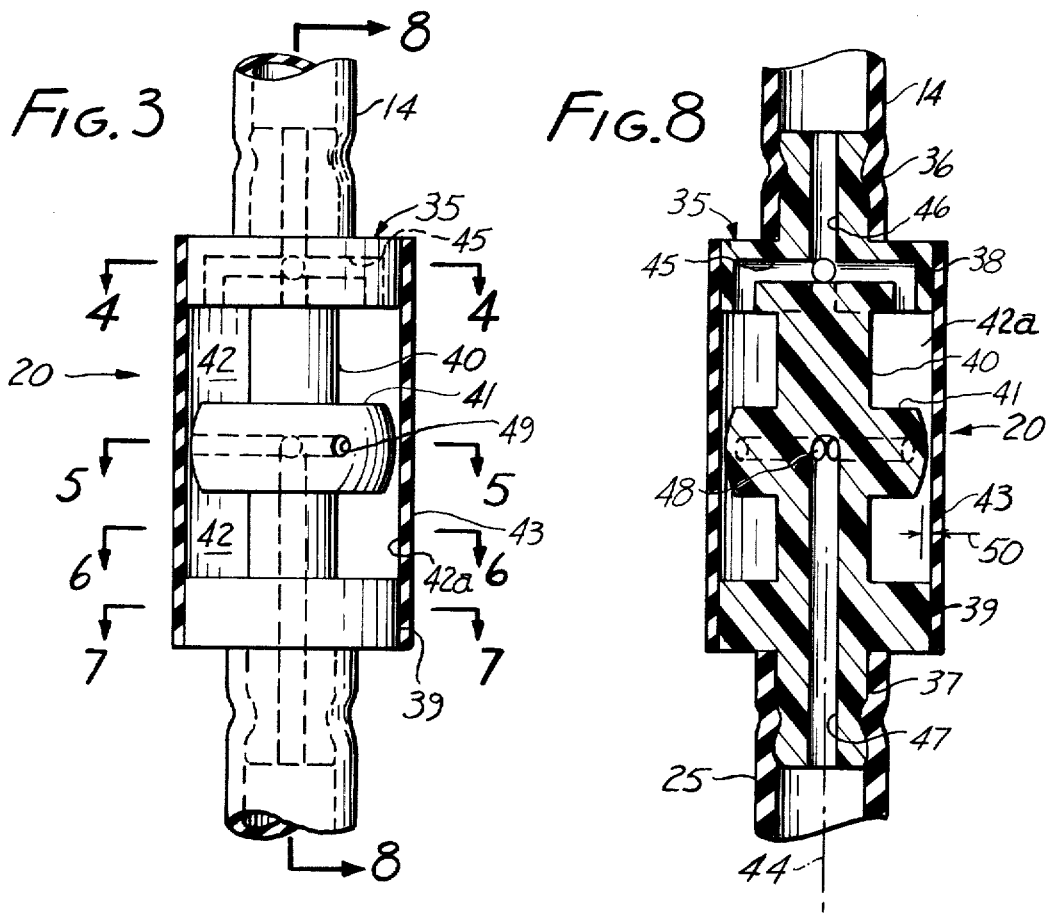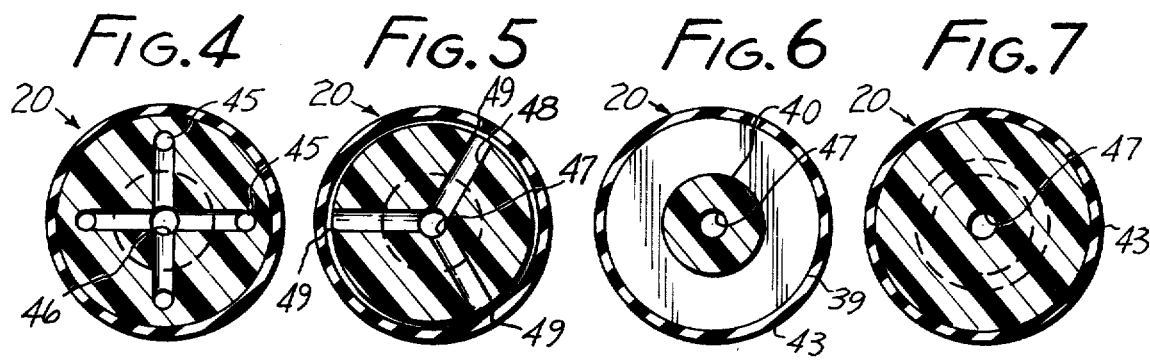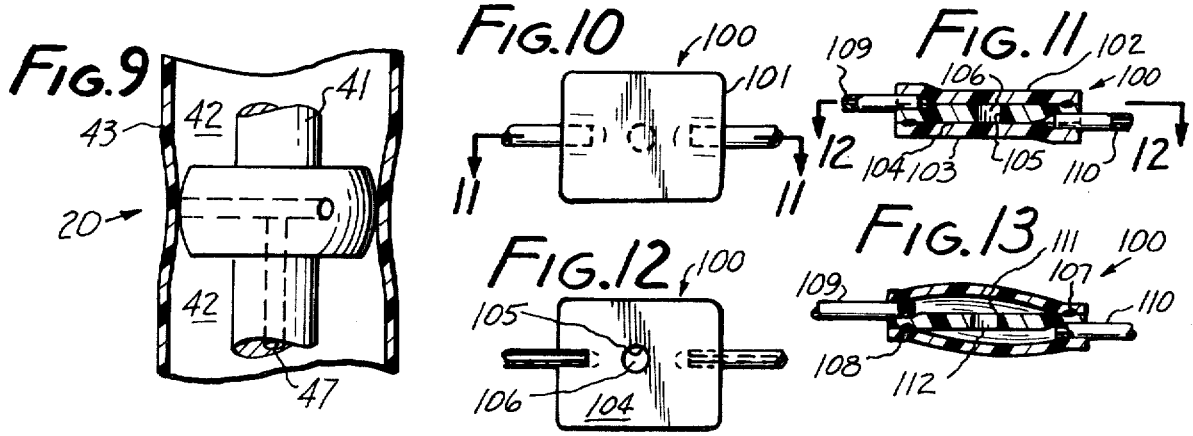

SHUNT SYSTEM RESISTANT TO OVERDRAINAGE AND SIPHONING AND VALVE THEREFOR

CROSS-REFERENCE TO OTHER APPLICATION

This is a continuation of applicant's presently copending U.S. patent application, Ser. No. 342,039, filed March 16, 1973, entitled "Shunt System Resistant to Overdrainage and Siphoning, and Valve Therefor", now abandoned.

This invention relates to physiological shunt systems and to a valve for preventing the shunt systems from overdraining or siphoning the region to be drained.

The usage of shunt systems to drain undesired fluids from one region of the human body to another has come into widespread use, especially in the treatment of ailments such as hydrocephalus. Hydrocephalus involves the inability of the human body properly to drain the fluid from the ventricles of the brain, and its accumulation under increasing pressures causes distressing and frequently fatal symptoms. A common technique for draining the excess fluid is that of shunting, wherein a collector tube, sometimes called a "catheter", is introduced into the ventricles of the brain, and then the shunt is directed either to the peritoneal cavity or to the atrium of the heart. In either case, the pressure of the origin and of the destination of the fluid is relatively close to that of atmosphere. In the course of its usage in a body, the position of the human body will be changed, for example, when the patient lies down and then stands up. As a consequence, the height of the column of liquid in the shunt system varies widely. When the patient stands up, the liquid column acts as a siphon which can result in overdrainage of the cerebral ventricles.

It is an object of this invention to provide a valve which will prevent a shunt system from excessively draining or siphoning fluid from a region to be drained, such as the ventricles of the brain. This is accomplished by interposing in the shunt system a valve whose flow condition, i.e., whether it permits or prevents flow through the shunt system, is determined by a pressure inside it as transmitted to it by the collector catheter (sometimes called a "collector tube.") and by the discharge catheter (sometimes called a "discharge tube"), and by a reference pressure which may be atmospheric pressure or some other known pressure. The valve includes movable closure means which, in the preferred embodiment, is a diaphragm movable in response to the differential between the pressure inside of and outside of the valve.

According to a preferred but optional feature of the invention, the movable closure means may comprise a diaphragm adapted to bear against a seat, and the diaphragm may have an "offset" relative to the seat which is a relative physical location of the two that requires a given differential pressure to be exerted on the diaphragm before the valve changes its flow condition.

According to a preferred construction of the valve, a tubular body is provided having a chamber with an open peripheral cylindrical boundary, the diaphragm being a tubular cylinder, and a seat located inside the diaphragm facing the tubular cylinder.

According to another construction of the valve, a pair of flexible diaphragms are disposed adjacent to opposite sides of a partition having a passage therethrough, which passage can be closed by either or both of said flexible diaphragms.

The above and other features of this invention will be fully understood from the following detailed description and the accompanying drawings in which:

FIG. 3 is a side view, partially in axial cross-section, showing the presently preferred embodiment of a valve according to the invention;

Figure 14:
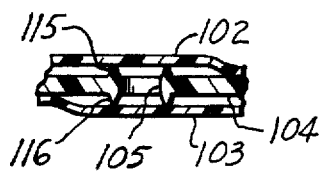

FIGS. 4, 5, 6 and 7 are cross-sections taken at lines 4—4, 5—5, 6—6, and 7—7, respectively, of FIG. 3;

FIG. 8 is an axial cross-section of the device of FIG. 3 in an open condition;

FIG. 9 is a fragmentary view of a portion of FIGS. 3 and 8 showing the device closed to flow;

FIG. 10 is a plan view of another embodiment of a valve for use in the invention;

FIGS. 11 and 12 are cross-sections taken at lines 11—11 and 12—12 of FIGS. 10 and 11, respectively;

FIG. 13 is a view taken the same as FIG. 11, but showing the valve in another flow condition; and FIG. 14 shows a modification of the valve of FIG. 10.

Figure 1:
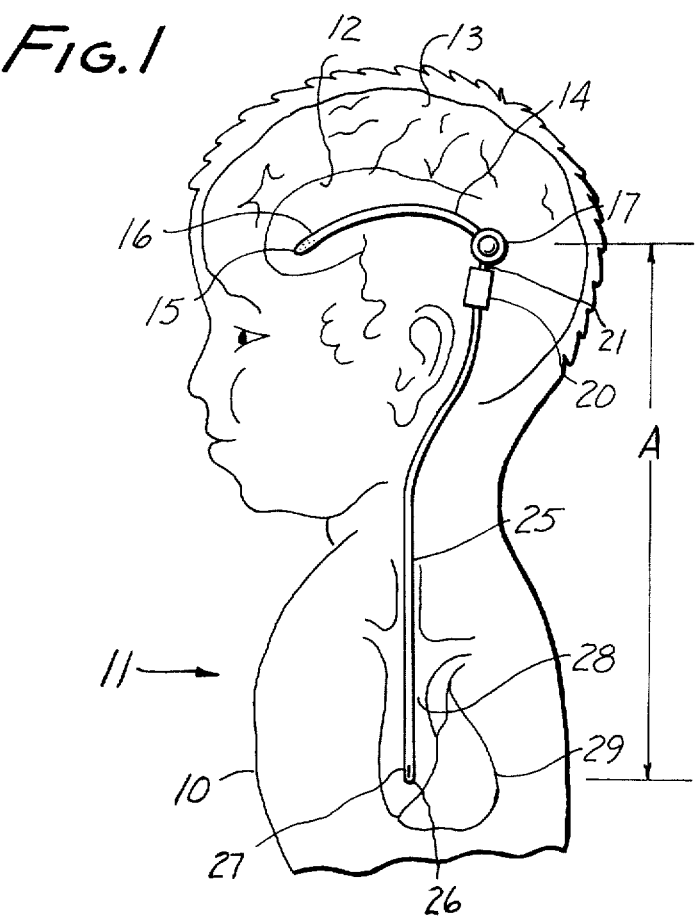
FIGS. 1 and 2 are two side views, partly in schematic notation, showing a shunt system according to the best mode contemplated of the invention in two relative positions of the body.

FIG. 1 shows the torso 10 of a human body 11, partially in cutaway and partly in schematic notation. Ventricles 12 of the brain 13 are shown into which a collector catheter 14 (sometimes called a collector tube) is placed for drainage of excessive fluid therefrom. The collector tube has been passed through an opening (not shown) drilled in the skull. Its open end 15 is disposed in the ventricles, and its other end is disposed outside the skull. Perforations 16 are provided for flow of liquid into the lumen of the collector tube. The collector tube extends downwardly and includes within it, if desired, a pump 17 of the type shown in U.S. Pat. No. 3,111,125 to Schulte, issued Nov. 19, 1963, entitled "Drainage Device". This pump and other circuit elements generally known in the art can optionally be used along with this invention.

The collector catheter (tube) includes a segment 21 which interconnects pump 17 to a valve 20 according to the invention. The valve joins the collector tube to a discharge catheter 25 (sometimes called a discharge tube), the lumen of which extends down to a tip 26 provided with a discharge slit 27 of the type shown in U.S. Pat. No. 3,020,913, issued to Heyer on Feb. 13, 1962, entitled "Surgical Drain". Suitable dispositions of the tubes in the human body are fully described in the aforesaid Schulte patent. Instead of the tip of the discharge tube being located in the atrium 28 of heart 29, it might instead be located in the peritoneal cavity. The ventricles are sometimes referred to as "a region of the human body to be drained", and the peritoneal cavity or the atrium of the heart is sometimes referred to as "a region into which the fluid is to be discharged".

Figure 2:
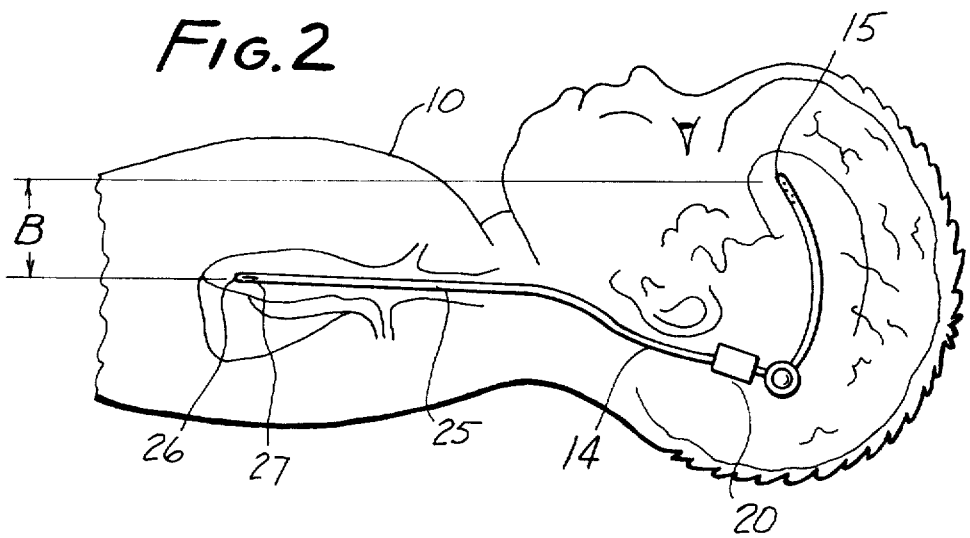

FIGS. 3 and 8 show a valve suitable for use in the system of FIGS. 1 and 2, wherein valve 20 is shown as including a valve body 35 having a pair of connectors 36, 37 to receive respectively segment 21 of collector tube 14 and the upper end of discharge tube 25. The valve body is preferably made generally cylindrical and has a pair of end flanges 38, 39 with cylindrical outer peripheries connected by a central post 40 which supports a seat member 41 between the two flanges. In the preferred construction of the invention, the diameters of the end flanges are equal and are greater than the greatest diameter of the seat member by an amount equal to twice an "offset" yet to be described.

There is formed between end flanges a chamber 42 which has an open peripheral cylindrical boundary 42a that is formed by a diaphragm 43 in the form of a tubular cylinder (when the cylinder is not distended or collapsed by differential fluid pressure). The valve body is made of rigid material, and the diaphragm is made of elastic resilient material such as medical grade silicone elastomer. The tubes may also be made of medical grade silicone elastomer. The diaphragm and the flanges are coaxial along central axis 44.

Collector ports 45 branch from a central passage 46 in connector 36 and flange 38 so as to open into chamber 42. Another central passage 47 passes through connector 37, flange 39, and post 40 to connect to discharge passage 48 in seat member 41. There may be three or more of these discharge passages which open into a respective seat 49, which seat immediately surrounds the opening of the passage. The seat member is crowned, so that seats 49 are located at the outermost periphery of the seat member 41.

Attention is now called to spacing 50 between the inside surface of the diaphragm and seats 49. This spacing is called the "offset" and expresses the distance between a pure cylinder extending between the end flanges, which is the position occupied by the diaphragm when there is no differential pressure across it, and seats 49. In the example shown, there is a clearance at this condition. However, the seat could instead contact the diaphragm, in which case the offset would be zero, or it might even indent into the diaphragm, in which case the offset would be negative. All of these conditions are referred to as the "offset" which will be more fully described below.

Diaphragm 43 comprises "movable closure means" in valve 20. The word "tube" herein is used completely interchangeably with the word "catheter".

FIGS. 10-13 show still another embodiment of a valve according to this invention. Valve 100 may be used in place of valve 20, and will perform the same functions. Valve 100 has a valve body 101 which is generally flat and preferably is rectangular, although it may be made in other shapes instead. It comprises a pair of flat flexible diaphragms 102, 103 which, in their undistended position, lie flat against a flat spacer 104. The spacer has a passage 105 therein which forms a cavity 106.

The spacer and two diaphragms are cemented together at peripheral joints 107, 108 which extend around their edges. An inlet passage 109 and an outlet passage 110 are sealed between the spacer and diaphragms 102 and 103, respectively. These passages are interchangeable as to use for inlet or outlet purposes. They open up into the region between the spacer and the respective diaphragm. The diaphragms form movable closure means in valve 100.

The intersections of passage 105 and the surfaces of the spacer form valve seats 111 and 112.

Spacer 104 may be made rigid, or may be as flexible as the diaphragms, as preferred. A suitable size for this device is approximately ½ × ¾ inch, the seam being approximately ⅛ inch wide, with diaphragms approximately 0.010 inch thick, and the spacers approximately 0.020 to 0.125 inch thick. The relative thicknesses are not proportionately shown in the drawings.

FIG. 14 shows a modification of FIG. 10, like parts bearing the same numbers. The only modification is that of providing the valve seats 115, 116 as crowned peripheral ring-shapes around the ends of passage 105.

The construction of the collector catheter and discharge catheter, and of the pump if used, are all fully described in the aforesaid Schulte patent, and no further discussion is provided here except to emphasize that the tubes have an internal lumen and are intended to constitute a drainage channel from one region of the human body to another. Items such as pump 17 and valve 20 are supplied to provide additional functions for this basic tubular circuit.

With respect to understanding the operation of the valve, one may assume for a moment that it is not present in FIGS. 1 and 2, but instead that the two tubes are connected together without its interposition and with the pump in an open position permitting free flow through the shunt system. In this case, it will be noted that, when the human body is erect as in FIG. 1, there is an elevation A between the inlet end of the collector tube and the outlet end of the discharge tube. When the human body is reclining, there is an elevation B between them which is less than A. There is, of course, a wide range of possible elevations between these points depending on the position of the human body, and the elevation might even be reduced to zero were the person to lie on his side with the two tips at substantially the same elevation. It is a fact that the ventricles of the brain, the atrium, and the peritoneal cavity operate at pressures which are relatively close to atmosphere, even though they may be somewhat different from one another. It is therefore evident from the foregoing considerations, and from the drawings, that changes in position of the body may cause a pumping or a siphoning action, especially when the person stands up, because the downstream suction exerted in the discharge tube will be very much greater in FIG. 1 than in FIG. 2. This is an action which, if permitted to continue, may overdrain the ventricles or such other region which is to be drained, and may, in the case of drainage of the ventricles, lead to headaches and depression of the fontanelle. It is the function of valve 20 and of the shunt system, of which it forms a part, to protect against this eventuality. It does so by subjecting the system to closure to flow in the event of undesirably low pressures relative to a reference pressure such as the atmosphere.

There are numerous regions in the human body which operate at atmospheric pressure, the regions beneath the skin and scalp being some of them. This is a relatively constant pressure for any given terrestial elevation, and it is also related to the pressures at both the collector and discharge ends of the system. It can, therefore, be used as a reference pressure by the valve. Alternatively, it is possible to encapsulate the valve within a charge of gas or fluid under pressure. In such event, the pressure of the fluid or gas would constitute a reference pressure. However, the simplest and most reliable system will utilize atmosphere as the "reference pressure" for the valve.

Accordingly, in FIG. 1 valve 20 is disposed in a region which operates at or near atmospheric pressure, such as beneath the scalp of the head as shown in the drawings, or at some other location which is also located between the elevations of the inlet end of the collector tube and the discharge end of the discharge tube when the person is erect. The diaphragm 43 in valve 20 comprises a movable closure means whose position is responsive to the differential between the fluid pressure in chamber 42, that is, the difference between the pressure inside the valve and the pressure on the outside of the diaphragm (the "reference pressure"). The pressure inside the chamber is a function of the pressures transmitted to it by the two tubes. Which tube provides the pressure of importance at any given time will later be discussed.

Consider first the arrangement shown in FIGS. 3–9. Assuming that there is not such an excessively low pressure in the discharge tube as would cause the diaphragm to be brought inwardly as shown in FIG. 9 to close the seats, the valve will be open to flow as shown in FIG. 3. Fluid will enter the collector ports 45, flow through the chamber 42, through seats 49, and out passages 47 and 48. This flow passes through the "offset" region, and will continue even in the presence of some negative differential pressure, until the pressure in the valve is sufficiently low to deflect the diaphragm inwardly by the offset distance to close the valve. Such a pressure will be transmitted to chamber 42 by the discharge tube. A suitable negative differential relative to reference pressure will cause the diaphragm to be brought against the seats (FIG. 9) and close them to prevent flow of fluid. This condition remains until the force exerted on that part of the diaphragm which is not occluded by the seats, and which is exposed only to pressure transmitted by the collector tube, becomes sufficient to overcome the force tending to hold the diaphragm against the seat. The valve will therefore block the system to flow until the downstream suction is relieved, such as by the patient's lying down, or until the valve is opened by a high enough pressure to overcome the closure.

In the human body, the rate of production of cerebrospinal fluid is substantially constant, as is the rate of drainage at a given pressure. The symptoms of hydrocephalus result because, when the drainage system is not permitting drainage at a proper rate and at an acceptable pressure, then in order to dispose of fluid at a rate substantially equal to its formation, the pressure rises to an intolerably high level.

Is is a function of valve 20 to close at unacceptably low downstream pressures. In so doing, however, it would be unacceptable for the valve to remain closed and trap unsuitably high pressures in the brain. It is an advantage of this valve that, even if the valve is closed by downstream suction, it will be opened without the development of excessive pressures in the ventricles when the force exerted on the diaphragm by the upstream pressure exceeds the force exerted as a consequence of downstream suction. This pressure relationship can be designed in the valve as a function of the various areas. Therefore, this is a safe valve which will not permit excessive upstream pressures to develop, while it protects against downstream suction.

Should the offset have been zero, the valve will normally remain closed to flow until a sufficient pressure is exerted in the chamber from the collector tube to balloon out the diaphragm to permit flow into the discharge passage.

Should the offset have been negative, i.e., the diaphragm be indented by the seat, then an even higher pressure would have to be exerted in the chamber from the collector tube to cause the valve to open to flow, and a somewhat lesser suction pressure will be required to close the valve.

The offset can thereby be selected to determine the amount of suction needed to close the valve and when the offset is zero or negative the amount of pressure to open it.

The valves of FIGS. 10–14 function in the same manner as the valve of FIG. 3. The normal condition of the valve is closed, as shown in FIGS. 11 and 14. However, upstream pressure will tend to balloon the regions between the spacers and the diaphragms, as shown in FIG. 13.

The valve seat of FIG. 14 can provide a more reliable seating surface for the diaphragm, and also a negative offset, if desired, by pressing into the diaphragms in a valve where the two diaphragms and spacer lie flat against one another. A positive offset can be provided by shimming the diaphragms away from the spacer by the desired distance.

When downstream suction is exerted, the tendency is to flatten the valve and close it. All of the pressure and functional considerations discussed with reference to the valve of FIG. 3 apply to valve 100.

This invention constitutes a shunt system: i.e., a collector tube and a discharge tube having its flow system provided with a valve with movable closure means that are actuated as a consequence of reference to pressures supplied to them from the said tubes and compared to a reference pressure such as atmosphere or some other known pressure source.

In addition to the design parameter of offset, the relationship between the positive force necessary to open a valve closed against suction can be varied by changing the total area of the seats which occlude the diaphragm when the diaphragm is brought against them compared to the area always exposed to the chamber pressure by changing their size or number. The greater the ratio of the latter area to the former area, the less upstream pressure is necessary to overcome the closure due to downstream suction. This parameter can be utilized to prevent an excessive opening pressure from developing when a suction exists at the discharge tube.

A suitable set of dimensions for valve 20 is as follows:

| | |
|---|---|
| Axial length of chamber 42: | ½" |
| Inside diameter of diaphragm 43: | 0.250 inch |
| Wall thickness of diaphragm 43: | 0.005–0.010" |
| Greatest outside diameter of seat member 41, depending on the size of the offset selected: | 0.250±.005 |
| Diameter of seats 49: | 0.040" |

The material of the diaphragm has the physical properties of medical grade silicone rubber elastomer about 0.005–0.010 inch thick.

In order to conform the terminology of the specification and claims, the following resume is provided.

"Outer wall means" in FIG. 3 comprises flanges 38 and 39 and tubular diaphragm 40. In FIG. 11, it comprises diaphragms 102 and 103, and the spacer between joints 107 and 108. The outer wall means form "chamber means". The chamber means in FIG. 3 is chamber 42. In FIG. 11, it is the regions between the diaphragms and the spacer, and within passage 105.

The outer wall means has a "flexible part". In FIG. 3, this part is the tubular diaphragm between flanges 38 and 39. In FIG. 11, it is the diaphragm areas inside joints 107 and 108.

The flexible parts are provided with "movable closure means". In FIG. 3, this is the inside surface of the tubular diaphragm which contacts the seat 49. In FIG. 11, it is the inside surface of the diaphragms which contact seats 111 and 112.

The "spacer means" disposed inside the chamber means is to provide something for the diaphragm to close on except itself. In FIG. 3, the spacer means is seat member 41. In FIG. 11, the spacer means is spacer 104.

The devices of FIGS. 10 and 14 illustrate that the spacer means need not be fully peripheral as in FIG. 1, but only need provide some arrangement whereby the movable closure means does not close upon itself.

The term "seat means" means something against which the movable closure means can bear to prevent flow through the valve. Seat 49 in FIG. 1 and seats 111 and 112 in FIG. 11 and seats 115 and 116 are examples of seat means. The seat means in the preferred construction surround a fluid passage which is closed by a diaphragm acting as movable closure means.

This is a differential pressure valve which closes when the difference between the fluid pressure inside the chamber means and the outside reference fluid pressure equals or exceeds some predetermined value, and opens when such is not the case.

This invention is not to be limited by the embodiments shown in the drawings and described in the description, which are given by way of example and not of limitation, but only in accordance with the scope of the appended claims.

I claim:

1. A drainage system for draining body fluid from a cavity in the human body comprising in combination: a surgically implantable collector catheter to receive fluid to be drained; a surgically implantable discharge catheter to discharge fluid drained by the collector catheter; and a surgically implantable valve interconnecting said catheters, said valve comprising imperforate outer wall means forming a chamber means, a collector passage and a discharge passage entering the chamber means through the outer wall means and connected respectively to the collector catheter and to the discharge catheter, at least part of the outer wall means being elastic and flexible, a spacer means in said chamber means, the elastic and flexible part of said outer wall means being provided with movable closure means located inside said chamber means, which movable closure means is so constructed and arranged as to be movable toward the spacer means to coact therewith to prevent flow through the valve, and to move away from the spacer means to permit such flow, said elastic and flexible part of said outer wall means being exposed on its side inside the chamber means only to pressure from the catheters, and on its side outside the chamber means only to a reference fluid pressure, the movable closure means closing the valve to flow when the difference between said pressures is equal to or greater that a predetermined value, and standing away from the spacer means to open the valve when the difference is less, the said part of the outer wall means being so disposed and arranged that said movement of said movable closure means is accompanied by elastic action of said part.

2. A drainage system for use in draining fluid from an upper region of the human body and discharging it into a lower region in the human body, the fluid pressure in said lower region approximating that of the atmosphere, said system comprising in combination: a surgically implantable collector catheter having one end for placement in the upper region, and its other end for placement outside of the said upper region; a surgically implantable discharge catheter having an end for placement where it will discharge into said lower region; and a surgically implantable valve to be disposed at an elevation between that of the upper region and of the lower region when the human body is erect, said valve to be disposed in an intermediate region of the human body whose fluid pressure approximates that of the atmosphere acting as a reference pressure, said valve fluidly interconnecting the catheters, said valve comprising imperforate outer wall means forming a chamber means, a collector passage and a discharge passage entering the chamber means through the outer wall means and connected respectively to the collector catheter and to the discharge catheter, at least part of the outer wall means being elastic and flexible, a spacer means in said chamber means, the said elastic and flexible part of said outer wall means being provided with movable closure means located inside said chamber means, which movable closure means is so constructed and arranged as to be movable toward the spacer means to coact therewith to prevent flow through the valve and to move away from the spacer means to permit such flow, said elastic and flexible part of said outer wall means being exposed on its side inside the chamber means only to pressure from the catheters, and on its side outside the chamber means only to said reference fluid pressure, the movable closure means closing the valve to flow when the difference between said pressures is equal to or greater than a predetermined value, and standing away from the spacer means to open the valve when the difference is less, the said part of the outer wall means being so disposed and arranged that said movement of said movable closure means is accompanied by elastic action of said part.

3. A drainage system according to claim 2 in which the movable closure means is the face of a diaphragm, said diaphragm comprising the elastic and flexible part of the outer wall means.

4. A drainage system according to claim 3 in which the chamber means has an open peripheral cylindrical boundary, in which the diaphragm is a tubular cylinder, and in which a seat is located on the spacer means inside the chamber means, faces the tubular cylinder, and is spaced therefrom when no differential pressure is exerted across the diaphragm, a pressure outside the diaphragm greater than the pressure in the chamber means tending to move the diaphragm toward the seat.

5. A drainage system according to claim 4 in which the collector catheter discharges into the chamber means outside of the seat, the area of the seat being less than the area of the diaphragm which is always exposed to pressure in the chamber means from the collector catheter.

6. A drainage system according to claim 1 in which the elastic and flexible part of the outer wall means comprises a pair of imperforate diaphragms which sandwich the spacer means between them, the spacer means and diaphragms being secured together to form the chamber means, there being a passage through the spacer means partially bounding the chamber means, and a valve seat at each end thereof, and in which the passages enter the region between the spacer means and a respective different one of the diaphragms.

7. A surgically implantable valve for use in the drainage of body fluid from a cavity in the human body wherein a collector catheter receives fluid to be drained, and a discharge catheter discharges fluid drained by the collector catheter, said valve being adapted to interconnect said catheters for preventing flow through the catheters when an excessive low fluid pressure relative to a reference fluid pressure exists in the valve, said valve comprising a chamber means having movable closure means adapted to be exposed on one side to pressure from the catheters, and on the other side to a reference fluid pressure, the valve being closed to flow when the pressure in the valve as transmitted to it by the catheters is sufficiently lower than the reference pressure, and open when such is not the case, said movable closure means being an imperforate elastic and flexible diaphragm, said chamber means having an open peripheral cylindrical boundary, the diaphragm being a tubular cylinder, and a valve seat means located inside the diaphragm facing the tubular cylinder, and spaced therefrom when no differential pressure is exerted across the diaphragm, a pressure outside the diaphragm greater than the pressure in the chamber means tending to move the diaphragm toward the seat means, the diaphragm being so disposed and arranged that its movements toward and away from the seat means are accompanied by elastic action of said diaphragm, a port opening into the chamber outside the seat means to connect to one catheter, and another port opening within the seat means to connect with the other catheter.

8. A surgically implantable valve for use in the drainage of body fluid from a cavity in the human body wherein a collector catheter receives fluid to be drained, and a discharge catheter discharges fluid drained by the collector catheter, said valve being adapted to interconnect said catheters for preventing flow through the catheters when an excessively low pressure exists in the valve relative to an external reference fluid pressure, said valve comprising movable closure means adapted to be exposed on one side to pressure from the catheters, and on the other side to said reference fluid pressure, the valve being closed to flow when the pressure in the valve as transmitted to it by the catheters is sufficiently lower than the reference fluid pressure, and open to flow when such is not the case, the valve comprising a pair of imperforate elastic and flexible diaphragms which sandwich a spacer means between them, the spacer means and diaphragm being secured together to form an enclosed chamber means, there being a passage through the spacer means partially bounding the chamber means, and a valve seat at each end thereof, and in which an inlet and an outlet passage enter the region between the spacer means and a respective different one of the diaphragms, the diaphragms comprising movable closure means adapted to open and to close the respective valve seats, and being so disposed and arranged that their movements toward and away from the valve seats are accompanied by elastic action of said diaphragms.

9. A drainage system for draining body fluid from a cavity in the human body comprising in combination: a surgically implantable collector catheter to receive fluid to be drained; a surgically implantable discharge catheter to discharge fluid drained by the collector catheter; and a surgically implantable valve interconnecting said catheters, said valve comprising imperforate outer wall means forming a chamber means, a collector passage and a discharge passage entering the chamber means through the outer wall means and connected respectively to the collector catheter and to the discharge catheter, at least part of the outer wall means being elastic and flexible, a seat means in said chamber means, said elastic and flexible part of said outer wall means being provided with movable closure means located inside said chamber means, which movable closure means is so constructed and arranged as to be movable toward the seat means to close the same and to prevent flow through the valve, and to move away from the seat means to permit such flow, said elastic and flexible part of said outer wall means being exposed on its side inside the chamber means only to pressure from the catheters, and on its side outside the chamber means only to a reference fluid pressure, the movable closure means closing the valve to flow when the difference between said pressures is equal to or greater than a predetermined value, and standing away from the seat means to open the valve when the difference is less, the said part of the outer wall means being so disposed and arranged that said movement of said movable closure means is accompanied by elastic action of said part.

10. A drainage system for use in draining fluid from an upper region of the human body and discharging it into a lower region in the human body, the fluid pressure in said lower region approximating that of the atmosphere, said system comprising in combination: a surgically implantable collector catheter having one end for placement in the upper region, and its other end for placement outside of the said upper region; a surgically implantable discharge catheter having an end for placement where it will discharge into said lower region; and a surgically implantable valve to be disposed at an elevation between that of the upper region and of the lower region when the human body is erect, said valve to be disposed in an intermediate region of the human body whose fluid pressure approximates that of the atmosphere acting as a reference pressure, said valve fluidly interconnecting the catheters, said valve comprising imperforate outer wall means forming a chamber means, a collector passage and a discharge passage entering the chamber means through the outer wall means and connected respectively to the collector catheter and to the discharge catheter, at least part of the outer wall means being elastic and flexible, a seat means in said chamber means, the flexible part of said outer wall means being provided with movable closure means located inside said chamber means, which movable closure is so constructed and arranged as to be movable toward the seat means to close the same and prevent flow through the valve and to move away from the seat means to permit such flow, said elastic and flexible part of said outer wall means being exposed on its side inside the chamber means only to pressure from the catheters, and on its side outside the chamber means only to said reference fluid pressure, the movable closure means closing the valve to flow when the difference between said pressures is equal to or greater than a predetermined value, and standing away from the seat means to open the valve when the difference is less, the said part of the outer wall means being so disposed and arranged that said movement of said movable closure means is accompanied by elastic action of said part.

11. A drainage system according to claim 10 in which the discharge passage opens into the seat means.

12. A drainage system according to claim 10 in which the collector catheter discharges into the chamber means outside of the seat means, the area of the seat means being less than the area of the movable closure means which is always exposed to pressure in the chamber means from the collector catheter.

* * * * *